(12) United States Patent
Wang et al.

(10) Patent No.: US 11,573,185 B2
(45) Date of Patent: Feb. 7, 2023

(54) METHOD AND DEVICE FOR DETECTING PYRETHROID PESTICIDE RESIDUES IN CROPS

(71) Applicant: Tobacco Research Institute of Chinese Academy of Agricultural Sciences, Shandong (CN)

(72) Inventors: Xiuguo Wang, Shandong (CN); Tong Liu, Shandong (CN); Dan Chen, Shandong (CN); Xiao Zheng, Shandong (CN); Guangjun Xu, Shandong (CN)

(73) Assignee: Tobacco Rsrch Inst. of Chinese Acad. of Ag. Sci., Shandong (CN)

( * ) Notice: Subject to any disclaimer, the term of this patent is extended or adjusted under 35 U.S.C. 154(b) by 140 days.

(21) Appl. No.: 17/213,496

(22) Filed: Mar. 26, 2021

(65) Prior Publication Data

US 2021/0381988 A1 Dec. 9, 2021

(30) Foreign Application Priority Data

Jun. 9, 2020 (CN) .......................... 202010518325.4

(51) Int. Cl.
| | |
|---|---|
| *G01N 21/78* | (2006.01) |
| *G01N 1/28* | (2006.01) |
| *G01N 1/34* | (2006.01) |
| *G01N 1/38* | (2006.01) |
| *G01N 21/27* | (2006.01) |
| *G01N 21/01* | (2006.01) |

(52) U.S. Cl.
CPC ............. *G01N 21/78* (2013.01); *G01N 1/286* (2013.01); *G01N 1/34* (2013.01); *G01N 1/38* (2013.01); *G01N 21/272* (2013.01); *G01N 2001/2866* (2013.01); *G01N 2001/386* (2013.01); *G01N 2021/0112* (2013.01); *G01N 2021/786* (2013.01)

(58) Field of Classification Search
CPC ...... G01N 21/78; G01N 21/272; G01N 1/286; G01N 1/34; G01N 1/38; G01N 2001/2866; G01N 2001/386; G01N 2021/0112; G01N 2021/786; G01N 33/5308; G01N 33/54388; G01N 33/558
See application file for complete search history.

(56) References Cited

U.S. PATENT DOCUMENTS 5,358,690 A * 10/1994 Guirguis ............... B01L 3/5021
436/63

* cited by examiner

*Primary Examiner* — Jennifer Wecker
*Assistant Examiner* — Alea N. Martin
(74) *Attorney, Agent, or Firm* — Dorsey & Whitney LLP

(57) ABSTRACT

A method and device for detecting pyrethroid pesticide residues in crops. Reaction membrane is arranged on a bottom plate and provided with a check-up line and a quality control line; a first mounting block and a second mounting block are arranged on the bottom plate; a first slide is arranged in the first mounting block, a second slide is arranged in the second mounting block; a sample pad and a bonding pad are arranged in the first slide; a water absorption pad is arranged in the second slide; a liquid inlet provided with a pipe is formed in the first mounting block, a pressing hole provided with a press block is formed in the second mounting block; protrusions are respectively formed on the pipe and the press block; sliding grooves are formed in the liquid inlet and the pressing hole; and first springs are arranged between the protrusions and the sliding grooves.

18 Claims, 5 Drawing Sheets

METHOD AND DEVICE FOR DETECTING PYRETHROID PESTICIDE RESIDUES IN CROPS

TECHNICAL FIELD

The present disclosure belongs to the technical field of devices for detecting residues, particularly relates to a method and device for detecting pyrethroid pesticide residues in crops.

BACKGROUND

Pyrethroid pesticides as broad-spectrum insecticides have quick actions, high efficiencies, low toxicity, less residues, and safety to crops and achieve remarkable effects on controlling 140 or more kinds of pests. Some pyrethroid pesticides achieve good effects on controlling underground pests and mites. The pyrethroid pesticides can cause nervous system diseases and skin diseases to human bodies if entering the human bodies via skin mucous membranes, respiratory tracts, or the like. Because of heavy use of the pyrethroid pesticides, potential neurotoxicity and mutagenicity of such pesticides are becoming more and more apparent, and resulting health risks and excessive residues in crops have been widely concerned. Thus, it is of great practical significance to strengthen monitoring of pyrethroid pesticide residues in crops.

Immunochromatography assays (ICAs) as emerging immunoassays in the 1990s fulfill rapid and accurate coloration through a dry chemical test strip by means of immunological and chromatographic antigen-antibody reaction to test substances. With development of medical clinical tests, a radioimmunoassay (RIA) represents the first generation, an enzyme-linked immunosorbent assay (ELISA) represents the second generation, and a rapid test strip for gold-labeled monoclonal antibodies represents the developing third generation.

In view of high requirements on on-site quick tests and demands of emergency disposal, the pyrethroid pesticide residues are tested increasingly by means of test strips for time-resolved fluorescence immunochromatography assays (TRFICAs). The accuracy in detection will be affected by high requirements on on-site tests and poor environmental conditions. Currently, samples are tested by the test strips for a long time, resulting in a serious influence on the efficiency of the on-site tests; and furthermore, a long detection process will affect a test result to a certain extent. Thus, it is necessary to put forward a method and device for detecting pyrethroid pesticide residues in crops, which can improve the detection efficiency.

SUMMARY

The objective of the present disclosure is to provide a method and device for detecting pyrethroid pesticide residues in crops, which can shorten the time for detecting the pyrethroid pesticide residues in crops, improve the detection efficiency, and prevent the accuracy of a test result from being affected by performing a test for a long time.

The present disclosure provides the following technical solutions.

A method and device for detecting pyrethroid pesticide residues in crops includes a bottom plate provided with a reaction membrane, where the reaction membrane is provided with a check-up line and a quality control line and has a concave structure; a first mounting block and a second mounting block are respectively arranged at two ends of the reaction membrane; a first slide is arranged in the first mounting block, and a second slide is arranged in the second mounting block; a sample pad and a bonding pad are arranged in the first slide and slidably connected to a side wall of the first slide; the bonding pad has a side face connected to one end of the reaction membrane and another side face connected to a side face of the sample pad; a water absorption pad is arranged in the second slide and slidably connected to a side wall of the second slide, and has a side face connected to the other end of the reaction membrane; a liquid inlet provided with a pipe is formed in the first mounting block, and a pressing hole provided with a press block is formed in the second mounting block; protrusions are respectively arranged on an external side wall of the pipe and a side wall of the press block; sliding grooves matched with the protrusions are formed in walls of the liquid inlet and the pressing hole; first springs are arranged between the protrusions and ends of the sliding grooves; and a cover plate is arranged between the first mounting block and the second mounting block.

Preferably, the first slide and the second slide are respectively composed of a straight portion and a bent portion which are connected at their ends.

Preferably, mounting pads are arranged between the reaction membrane and the bonding pad and between the reaction membrane and the water absorption pad.

Preferably, first grooves in the first mounting block and the second mounting block are matched with the mounting pads and have bottoms slidably connected to the mounting pads.

Preferably, a first sealing plug on the first mounting block and a second sealing plug on the second mounting block respectively have an edge slidably connected to a side wall of the corresponding straight portion and a bottom of the corresponding first groove.

Preferably, expansion plates and second grooves matched with the expansion plates are arranged at ends of the cover plate, and clamping grooves in the first mounting block and the second mounting block are matched with the expansion plates and slidably connected to the expansion plates; the expansion plates are slidably connected to walls of the second grooves; and second springs are arranged between the expansion plates and bottoms of the second grooves.

Preferably, stop plates are arranged at ends of the expansion plates; third grooves in walls of the second grooves are matched with the stop plates and have walls slidably connected to edges of the stop plates; and two ends of each said second spring are respectively connected to the corresponding stop plate and a bottom of the corresponding third groove.

Preferably, a clamping plate is arranged at lower ends of the first mounting block and the second mounting block, and a clamping protrusion having a circular longitudinal section is formed on a side wall of the clamping plate.

Preferably, a fourth groove is formed in the bottom plate, and a clamping hole matched with the clamping protrusion is formed in a wall of the fourth groove.

The present disclosure has the following beneficial effects:

a concave reaction membrane is arranged on a bottom plate and provided with a check-up line and a quality control line; in this case, a sample to be tested can quickly flow into the reaction membrane, so that the detection efficiency is improved;

a first mounting block and a second mounting block are respectively arranged at two ends of the reaction membrane;

a first slide is arranged in the first mounting block, and a second slide is arranged in the second mounting block; a sample pad and a bonding pad are arranged in the first slide and slidably connected to a side wall of the first slide; the bonding pad has one side face connected to one end of the reaction membrane and the other side face connected to a side face of the sample pad; a water absorption pad in the second slide is slidably connected to a side wall of the second slide and has a side face connected to the other end of the reaction membrane; the whole side face of the bonding pad and the whole side face of the water absorption pad are connected to the reaction membrane, and in this way, a contact area of the bonding pad and the reaction membrane as well as a contact area of the water absorption pad and the reaction membrane is increased, so that the detection efficiency is improved; and the sample pad and the bonding pad can be conveniently arranged through the first slide, and the water absorption pad can be conveniently arranged through the second slide;

a liquid inlet provided with a pipe is formed in the first mounting block, and a pressing hole provided with a press block is formed in the second mounting block; protrusions are respectively formed on an external side wall of the pipe and a side wall of the press block; sliding grooves matched with the protrusions are formed in walls of the liquid inlet and the pressing hole; first springs are arranged between the protrusions and ends of the sliding grooves; the pipe can be prevented, by the corresponding protrusion and sliding groove, from disengaging from the liquid inlet, and the press block can be prevented, by the corresponding protrusion and sliding groove, from disengaging from the pressing hole; the pipe can moderately press the sample pad by means of the corresponding first spring having a proper elastic coefficient to avoid a gap between the sample pad and the reaction membrane and a gap between the bonding pad and the reaction membrane; and the press block can moderately press the water absorption pad by means of the corresponding first spring having a proper elastic coefficient to avoid a gap between the water absorption pad and the reaction membrane; and a cover plate between the first mounting block and the second mounting block provides a closed detection environment to prevent external environmental conditions from affecting a test result.

BRIEF DESCRIPTION OF DRAWINGS

The accompanying drawings are used to provide further understanding of the present disclosure and constitute a part of the specification. The accompanying drawings, together with the embodiments of the present disclosure, are used to explain the present disclosure but do not pose a limitation to the present disclosure. In the accompanying drawings.

Figure 1:
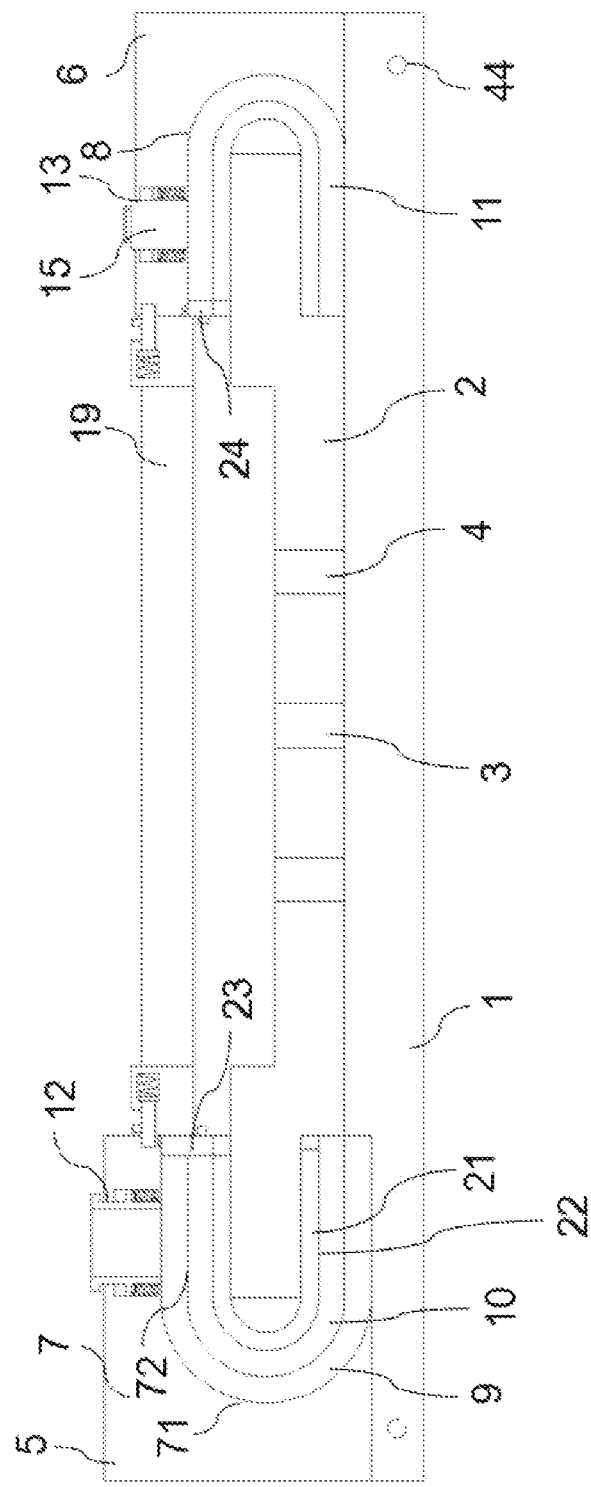
FIG. 1 is a structural diagram of the present disclosure.
Figure 2:
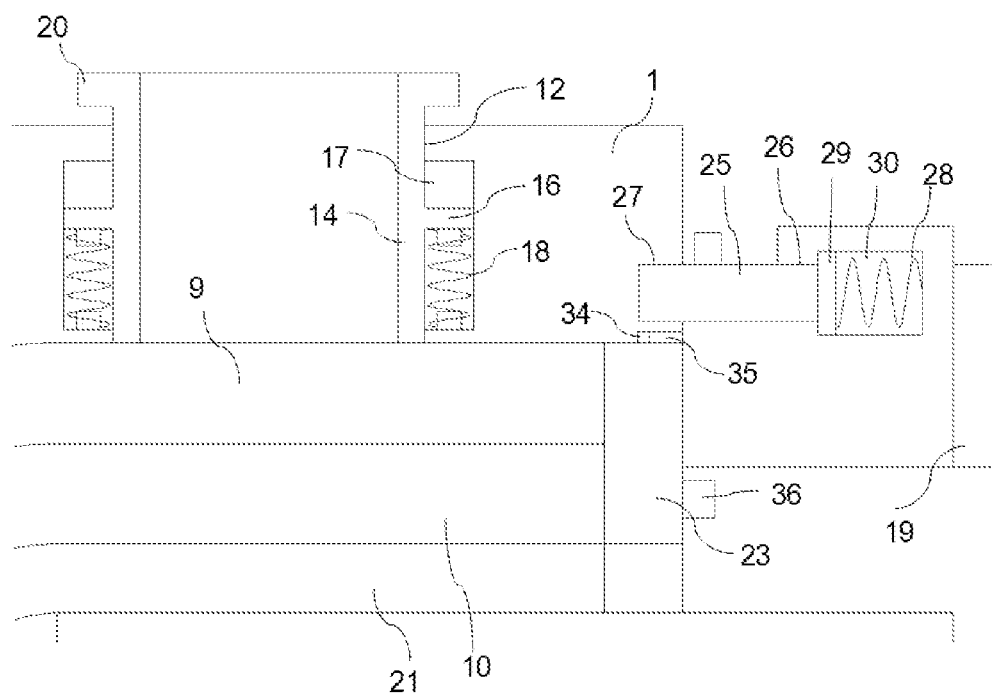
FIG. 2 is an enlarged partial diagram of the present disclosure.
Figure 3:
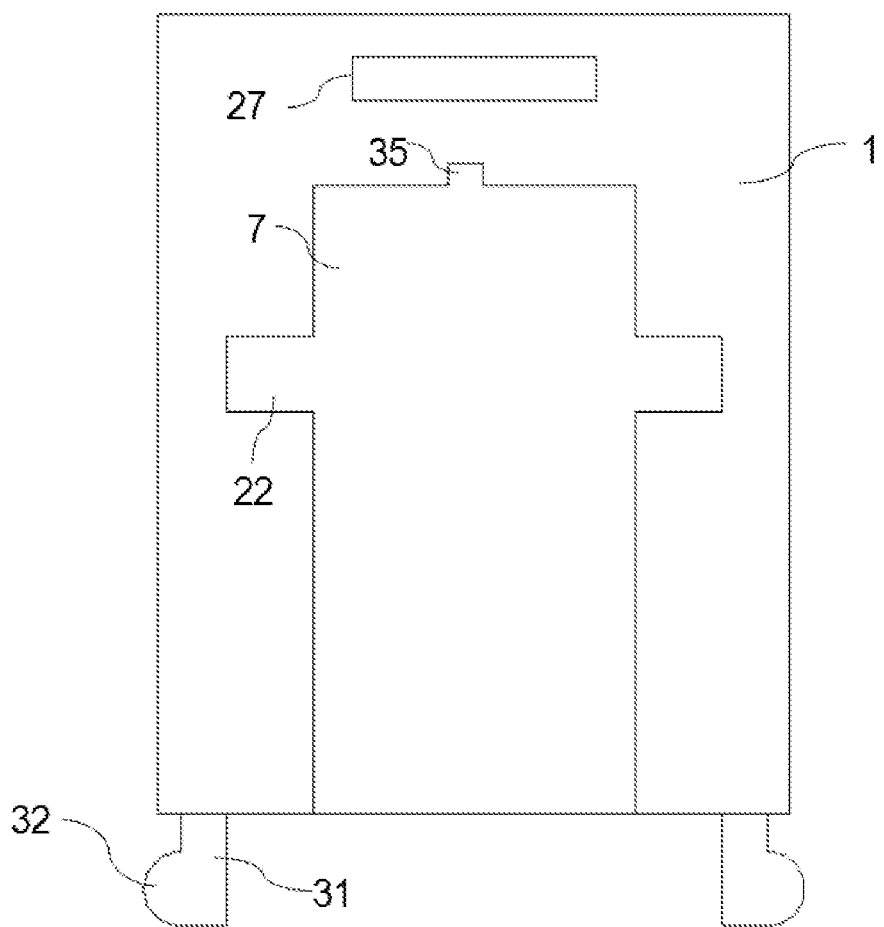
FIG. 3 is a side view of a first mounting block of the present disclosure.
Figure 4:
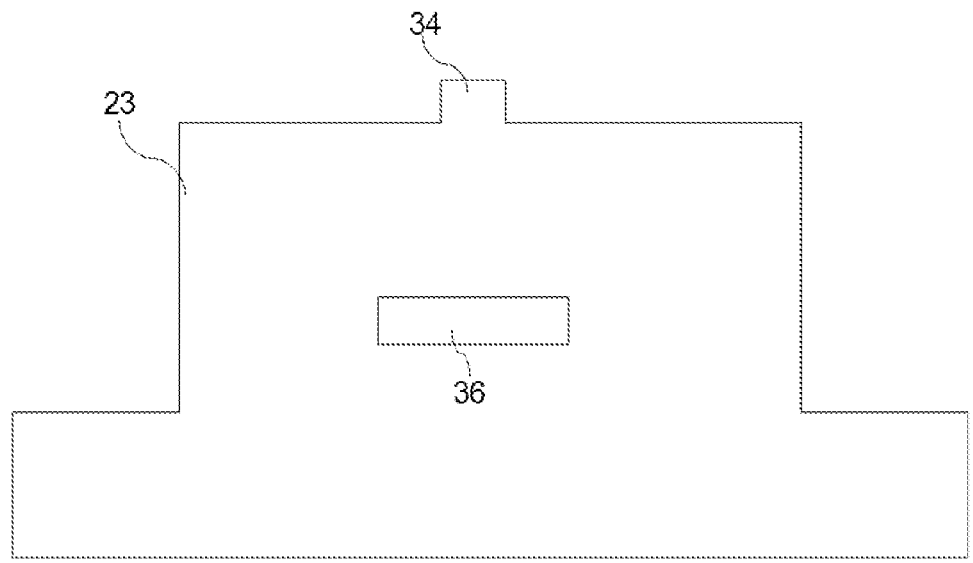
FIG. 4 is a side view of a first sealing plug of the present disclosure.
Figure 5:
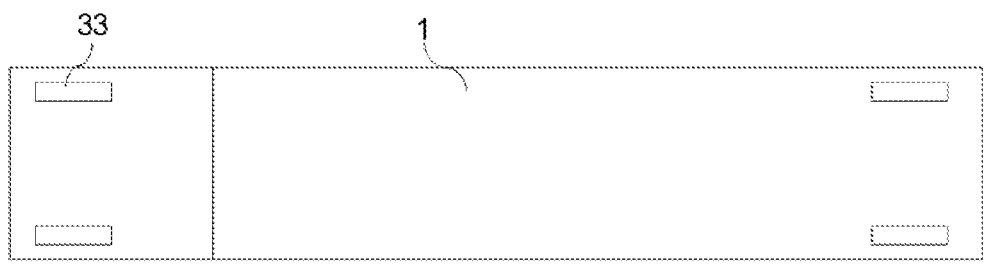
FIG. 5 is a top view of a bottom plate of the present disclosure.

In the figure, 1. bottom plate, 2. reaction membrane, 3. check-up line, 4. quality control line, 5. first mounting block, 6. second mounting block, 7. first slide, 71. bent portion, 72. straight portion, 8. second slide, 9. sample pad, 10. bonding pad, 11. water absorption pad, 12. liquid inlet, 13. pressing hole, 14. pipe, 15. press block, 16. protrusion, 17. sliding groove, 18. first spring, 19. cover plate, 20. annular protrusion, 21. mounting pad, 22. first groove, 23. first sealing plug, 24. second sealing plug, 25. expansion plate, 26. second groove, 27. clamping groove, 28. second spring, 29. stop plate, 30. third groove, 31. clamping plate, 32. clamping protrusion, 33. fourth groove, 34. limiting protrusion, 35. limiting groove, 36. grab bar, 37. internal thread, 38. external thread, 39. lifting rod, 40. lifting hole, 41. protection plate, 42. clamping plate, 43. recess, 44. clamping hole.

DETAILED DESCRIPTION

Embodiment 1

According to a method and device for detecting pyrethroid pesticide residues in crops, as shown in FIG. 1 to FIG. 5, a concave reaction membrane 2 is arranged on a bottom plate 1 and provided with a check-up line 3 and a quality control line 4, and two ends thereof are higher than its middle by a thickness of the reaction membrane 2. In this case, a sample to be tested can quickly flow into the reaction membrane, so that the detection efficiency is improved; a first mounting block 5 and a second mounting block 6 are respectively arranged at two ends of the reaction membrane 2, and two clamping plates 31 are arranged at the lower end of the first mounting block 5 as well as the lower end of the second mounting block 6 in the vertical direction; upper ends of the clamping plates 31 are connected to the first mounting block 5 as well as the second mounting block 6, and clamping protrusions 32 having circular longitudinal sections are formed on external side walls of the clamping plates 31; fourth grooves 33 are formed in the upper end of the bottom plate 1, and clamping holes 44 matched with the clamping protrusions 32 are formed in walls of the fourth grooves 33; the first mounting block 5 and the second mounting block 6 are connected to the bottom plate 1 more stably through the fixing plates 31 and the fourth grooves 33; and the fixing plates 31 can be prevented, by the clamping protrusions 32 and the clamping holes 44, from disengaging from the fourth grooves 33.

A first slide 7 in the first mounting block 5 and a second slide 8 in the second mounting block 6 are respectively composed of a straight portion 72 and a bent portion 71 which are connected at their ends; a sample pad 9 and a bonding pad 10 are arranged in the first slide 7 and slidably connected to a side wall of the first slide 7; the bonding pad 10 has one side face connected to one end of the reaction membrane 2 and the other side face connected to a side face of the sample pad 9; the sample pad 9 and the bonding pad 10 are facilitated, by the first slide 7, to be bent to wrap one end of the reaction membrane 2; a water absorption pad 11 in the second slide 8 is slidably connected to a side wall of the second slide 8 and has a side face connected to the other end of the reaction membrane 2; the water absorption pad is facilitated, by the second slide 8, to be bent to wrap the other end of the reaction membrane 2; the whole side face of the bonding pad 10 and the whole side face of the water absorption pad 11 are connected to the reaction membrane 2; and in this way, a contact area of the bonding pad 10 and the reaction membrane 2 as well as a contact area of the water absorption pad 11 and the reaction membrane 2 is increased, so that the detection efficiency is improved.

Mounting pads 21 are arranged between the reaction membrane 2 and the bonding pad 10 and between the reaction membrane 2 and the water absorption pad 11; first grooves 22 in the first mounting block 5 and the second mounting block 6 are matched with the mounting pads 21 and have bottoms slidably connected to the mounting pads 21; the sample pad 9 and the bonding pad 10 are facilitated, by the corresponding mounting pad 21, to slide along the first slide 7, and the water absorption pad 11 is facilitated, by the corresponding mounting pad 21, to slide along the second slide 8; a first sealing plug 23 on the first mounting block 5 and a second sealing plug 24 on the second mounting block 6 respectively have an edge slidably connected to a side wall of the corresponding straight portion 72 and the bottom of the corresponding first groove 22; the sample pad 9 and the bonding pad 10 can be prevented, by the first sealing plug 23, from disengaging from the first slide 7, and the water absorption pad 11 can be prevented, by the second sealing plug 24, from disengaging from the second slide 8; limiting protrusions 34 at upper ends of the first sealing plug 23 and the second sealing plug 24 are slidably connected to bottoms of limiting grooves 35, matched with the limiting protrusions 34, in the first mounting block 5 and the second mounting block 6, and the distance of the first sealing plug 23 sliding into the first slide 7 and the distance of the second sealing plug 24 sliding into the second slide 8 can be limited by the limiting protrusions 34 and the limiting grooves 35; a grab bar 36 having two ends connected to the first sealing plug 23 is arranged on a side wall of the first sealing plug 23, and a grab bar 36 having two ends connected to the second sealing plug 24 is arranged on a side wall of the second sealing plug 24; and the first sealing plug 23 and the second sealing plug 24 can be conveniently grabbed through the grab bars 36.

A liquid inlet 12 communicated with the first slide 7 and provided with a pipe 14 is formed in the first mounting block 5, and a pressing hole 13 communicated with the second slide 8 and provided with a press block 15 is formed in the second mounting block 6; an external side wall of the pipe 14 is slidably connected to the wall of the liquid inlet 12, and a side wall of the press block 15 is slidably connected to the wall of the pressing hole 13; an annular protrusion 20 is formed on an external side wall of the upper end of the pipe 14 to make the pipe 14 be grabbed conveniently; protrusions 16 are formed on the external side wall of the pipe 14 and the side wall of the press block 15; sliding grooves 17 matched with the protrusions 16 are formed on the walls of the liquid inlet 12 and the pressing hole 13; first springs 18 are arranged between the protrusions 16 and ends of the sliding grooves 17 and respectively have two ends connected to the corresponding protrusion 16 and the lower end of the corresponding sliding groove 17; the pipe 14 can be prevented, by the corresponding protrusion 16 and sliding groove 17, from disengaging from the liquid inlet 12, and the press block 15 can be prevented, by the corresponding protrusion 16 and sliding groove 17, from disengaging from the pressing hole 13; the pipe 14 presses the sample pad 9 by means of the corresponding first spring 18 to avoid a gap between the sample pad 9 and the reaction membrane 2 and a gap between the bonding pad 10 and the reaction membrane 2; and the press block 15 presses the water absorption pad 11 by means of the corresponding first spring 18 to avoid a gap between the water absorption pad 11 and the reaction membrane 2.

A cover plate 19 between the first mounting block 5 and the second mounting block 6 provides a closed detection environment to prevent external environmental factors from affecting a test result; expansion plates 25 and second grooves 26 matched with the expansion plates 25 are arranged at two ends of the cover plate 19, and clamping grooves 27 in the first mounting block 5 and the second mounting block 6 are matched with the expansion plates 25 and have walls slidably connected to the expansion plates 25; second springs 28 are arranged between the expansion plates 25 and bottoms of the second grooves 26; the expansion plates 25 slide more stably via the second grooves 26; the cover plate 19 is fixed to the first mounting block 5 and the second mounting block 6 more firmly via the clamping grooves 27; stop plates 29 having end faces connected to the expansion plates 25 are arranged at one ends of the expansion plates 25; third grooves 30 in walls of the second grooves 26 are matched with the stop plates 29 and have walls slidably connected to edges of the stop plates 29; two ends of each second spring 28 are respectively connected to the corresponding stop plate 29 and the bottom of the corresponding third groove 30; and the expansion plates 25 can be prevented, by the stop plates 29 and the third grooves 30, from disengaging from the second grooves 26.

Embodiment 2

Figure 6:
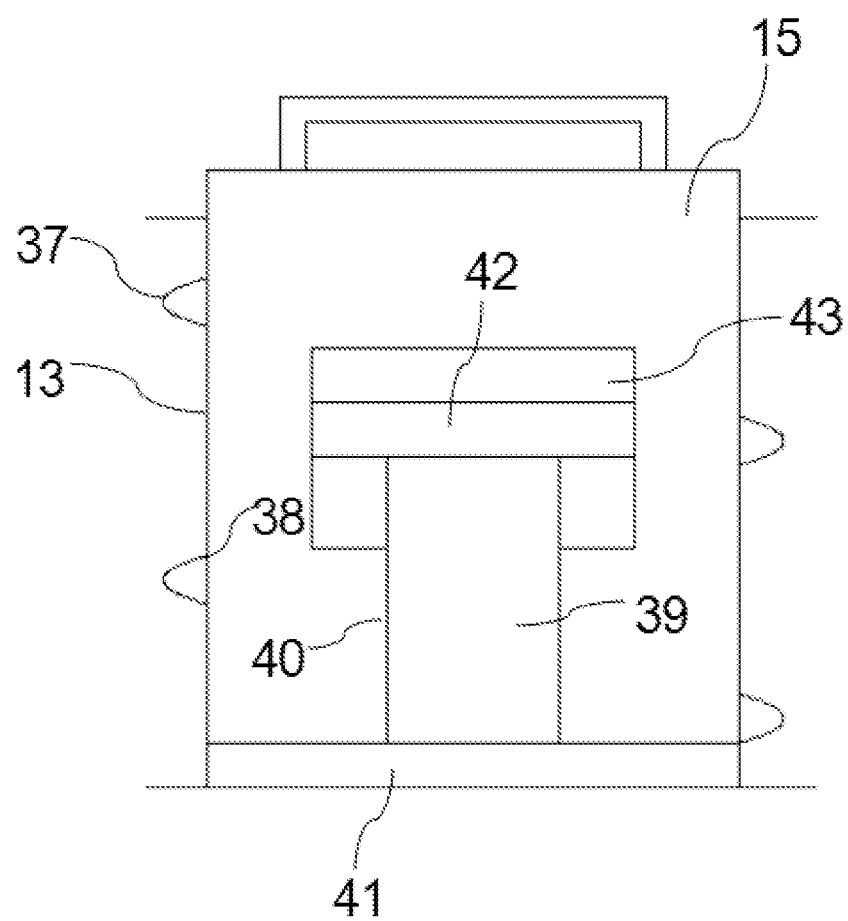
FIG. 6 is a structural diagram of a press block of the present disclosure.

As shown in FIG. 6, an external thread 38 is arranged on the side wall of the press block 15, an internal thread 37 matched with the external thread 38 is arranged on the wall of the pressing hole 13, and the press block 15 is in threaded connection with the pressing hole and is fixed more firmly through the internal thread 37 and the external thread 38; a lifting rod 39 and a lifting hole 40 which is matched with the lifting rod 39 and has a wall slidably connected to a side wall of the lifting rod 39 are arranged at the lower end of the press block 15 in the vertical direction; a clamping plate 42 having a lower end face connected to the lifting rod 39 is arranged at the upper end of the lifting rod 39, and a protection plate 41 having an upper end face connected to the lifting rod 39 and rotationally connected to the press block 15 is arrange at the lower end of the lifting rod 39; a recess 43 in the press block 15 is matched with the clamping plate 42 and has a wall slidably connected to the edge of the clamping plate 42; the press block 15 can be prevented, by the protection plate 41, from damaging the water absorption pad 11 when rotating; and the lifting rod 39 can be prevented, by the clamping plate 42 and the recess 43, from disengaging from the lifting hole 40.

The operating mode of the present disclosure is as follows: the first mounting block 5 and the second mounting block 6 are arranged on the bottom plate 1; the clamping plates 31 are inserted into the fourth grooves 33, and the clamping protrusions 32 are inserted into the clamping holes 44; the mounting pads 21 slide into the first grooves 22; the reaction membrane 2 having the two ends connected to the mounting pads 21 is arranged on the bottom plate 1; the pipe 14 is upwards pulled to make the sample pad 9 and the bonding pad 10 slide into the first slide 7; the press block 15 is upwards pulled to make the water absorption pad 11 slide into the second slide 8; the mounting pads 21 are pulled out, and the pipe 14 and the press block 15 are downwards pulled; the first sealing plug 23 is inserted into the first slide 7, and the second sealing plug 24 is inserted into the second slide 8; the expansion plates 25 are pushed to be inserted into the clamping grooves 27; the whole side face of the bonding pad 10 and the whole side face of the water absorption pad 11 are connected to the reaction membrane 2, and in this way, the contact area of the bonding pad 10 and the reaction membrane 2 as well as the contact area of the water absorption pad 11 and the reaction membrane 2 is increased, so that the detection efficiency is improved; the pipe 14 presses the sample pad 9 by means of the corresponding first spring 18 to avoid the gap between the sample pad 9 and the reaction membrane 2 and the gap between the bonding pad 10 and the reaction membrane 2, and the press block 15 presses the water absorption pad 11 by means of the corresponding first spring 18 to avoid the gap between the water absorption pad 11 and the reaction membrane 2; and the cover plate 19 provides the closed detection environment to prevent the external environmental factors from affecting the test result.

The above embodiments are only preferred ones, and are not intended to limit the present disclosure. Although the present disclosure is expounded with reference to the above embodiments, a person skilled in the art can still make modifications on the technical solutions recorded in the above embodiments or equivalent substitutions on some technical features of the technical solutions. Any modifications, equivalent substitutions, improvements, and the like made without deviating from the spirit and principle of the present disclosure should fall within the protection scope of the present disclosure.

What is claimed is:

1. A device for detecting pyrethroid pesticide residues in crops, the device comprising:
   a bottom plate provided with a reaction membrane, wherein the reaction membrane is provided with a check-up line and a quality control line and has a concave structure;
   a first mounting block and a second mounting block are respectively arranged at two ends of the reaction membrane;
   a first slide is arranged in the first mounting block, and a second slide is arranged in the second mounting block;
   a sample pad and a bonding pad are arranged in the first slide and slidably connected to a side wall of the first slide; the bonding pad has a side face connected to one end of the reaction membrane and another side face connected to a side face of the sample pad;
   a water absorption pad is arranged in the second slide and slidably connected to a side wall of the second slide, and has a side face connected to the other end of the reaction membrane;
   a liquid inlet provided with a pipe is formed in the first mounting block, and a pressing hole provided with a press block is formed in the second mounting block;
   protrusions are respectively arranged on an external side wall of the pipe and a side wall of the press block;
   sliding grooves matched with the protrusions are formed in walls of the liquid inlet and the pressing hole;
   first springs are arranged between the protrusions and ends of the sliding grooves; and
   a cover plate is arranged between the first mounting block and the second mounting block.

2. The device according to claim 1, wherein the first slide and the second slide are respectively composed of a straight portion and a bent portion which are connected at their ends.

3. The device according to claim 2, wherein mounting pads are arranged between the reaction membrane and the bonding pad and between the reaction membrane and the water absorption pad.

4. The device according to claim 3, wherein first grooves in the first mounting block and the second mounting block are matched with the mounting pads and have bottoms slidably connected to the mounting pads.

5. The device according to claim 4, wherein a first sealing plug on the first mounting block and a second sealing plug on the second mounting block respectively have an edge slidably connected to a side wall of the corresponding straight portion and a bottom of the corresponding first groove.

6. The device according to claim 1, wherein expansion plates and second grooves matched with the expansion plates are arranged at ends of the cover plate, and clamping grooves in the first mounting block and the second mounting block are matched with the expansion plates and slidably connected to the expansion plates; the expansion plates are slidably connected to walls of the second grooves; and second springs are arranged between the expansion plates and bottoms of the second grooves.

7. The device according to claim 6, wherein stop plates are arranged at ends of the expansion plates; third grooves in walls of the second grooves are matched with the stop plates and have walls slidably connected to edges of the stop plates; and two ends of each said second spring are respectively connected to the corresponding stop plate and a bottom of the corresponding third groove.

8. The device according to claim 1, wherein a clamping plate is arranged at lower ends of the first mounting block and the second mounting block, and a clamping protrusion having a circular longitudinal section is formed on a side wall of the clamping plate.

9. The device according to claim 8, wherein a fourth groove is formed in the bottom plate, and a clamping hole matched with the clamping protrusion is formed in a wall of the fourth groove.

10. A method for detecting pyrethroid pesticide residues in crops by using the device according to claim 1, the method comprising:
    S1: arranging the first mounting block and the second mounting block onto the bottom plate;
    S2: sliding the mounting pads into the first grooves, and arranging the reaction membrane onto the bottom plate to make the two ends of the reaction membrane be connected to the mounting pads;
    S3: upwards pulling the pipe to make the sample pad and the bonding pad slide into the first slide; pulling out the mounting pads, downwards pulling the pipe, inserting the first sealing plug, and upwards pulling the press block to make the water absorption pad slide into the second slide; pulling out the mounting pads, downwards pulling the press block, and inserting the second sealing plug; and
    S4: pushing the expansion plates to make the expansion plates be inserted into the clamping grooves.

11. A method for detecting pyrethroid pesticide residues in crops by using the device according to claim 2, the method comprising:
    S1: arranging the first mounting block and the second mounting block onto the bottom plate;
    S2: sliding the mounting pads into the first grooves, and arranging the reaction membrane onto the bottom plate to make the two ends of the reaction membrane be connected to the mounting pads;
    S3: upwards pulling the pipe to make the sample pad and the bonding pad slide into the first slide; pulling out the mounting pads, downwards pulling the pipe, inserting the first sealing plug, and upwards pulling the press block to make the water absorption pad slide into the second slide; pulling out the mounting pads, downwards pulling the press block, and inserting the second sealing plug; and
    S4: pushing the expansion plates to make the expansion plates be inserted into the clamping grooves.

12. A method for detecting pyrethroid pesticide residues in crops by using the device according to claim 3, the method comprising:
- S1: arranging the first mounting block and the second mounting block onto the bottom plate;
- S2: sliding the mounting pads into the first grooves, and arranging the reaction membrane onto the bottom plate to make the two ends of the reaction membrane be connected to the mounting pads;
- S3: upwards pulling the pipe to make the sample pad and the bonding pad slide into the first slide; pulling out the mounting pads, downwards pulling the pipe, inserting the first sealing plug, and upwards pulling the press block to make the water absorption pad slide into the second slide; pulling out the mounting pads, downwards pulling the press block, and inserting the second sealing plug; and
- S4: pushing the expansion plates to make the expansion plates be inserted into the clamping grooves.

13. A method for detecting pyrethroid pesticide residues in crops by using the device according to claim 4, the method comprising:
- S1: arranging the first mounting block and the second mounting block onto the bottom plate;
- S2: sliding the mounting pads into the first grooves, and arranging the reaction membrane onto the bottom plate to make the two ends of the reaction membrane be connected to the mounting pads;
- S3: upwards pulling the pipe to make the sample pad and the bonding pad slide into the first slide; pulling out the mounting pads, downwards pulling the pipe, inserting the first sealing plug, and upwards pulling the press block to make the water absorption pad slide into the second slide; pulling out the mounting pads, downwards pulling the press block, and inserting the second sealing plug; and
- S4: pushing the expansion plates to make the expansion plates be inserted into the clamping grooves.

14. A method for detecting pyrethroid pesticide residues in crops by using the device according to claim 5, the method comprising:
- S1: arranging the first mounting block and the second mounting block onto the bottom plate;
- S2: sliding the mounting pads into the first grooves, and arranging the reaction membrane onto the bottom plate to make the two ends of the reaction membrane be connected to the mounting pads;
- S3: upwards pulling the pipe to make the sample pad and the bonding pad slide into the first slide; pulling out the mounting pads, downwards pulling the pipe, inserting the first sealing plug, and upwards pulling the press block to make the water absorption pad slide into the second slide; pulling out the mounting pads, downwards pulling the press block, and inserting the second sealing plug; and
- S4: pushing the expansion plates to make the expansion plates be inserted into the clamping grooves.

15. A method for detecting pyrethroid pesticide residues in crops by using the device according to claim 6, the method comprising:
- S1: arranging the first mounting block and the second mounting block onto the bottom plate;
- S2: sliding the mounting pads into the first grooves, and arranging the reaction membrane onto the bottom plate to make the two ends of the reaction membrane be connected to the mounting pads;
- S3: upwards pulling the pipe to make the sample pad and the bonding pad slide into the first slide; pulling out the mounting pads, downwards pulling the pipe, inserting the first sealing plug, and upwards pulling the press block to make the water absorption pad slide into the second slide; pulling out the mounting pads, downwards pulling the press block, and inserting the second sealing plug; and
- S4: pushing the expansion plates to make the expansion plates be inserted into the clamping grooves.

16. A method for detecting pyrethroid pesticide residues in crops by using the device according to claim 7, the method comprising:
- S1: arranging the first mounting block and the second mounting block onto the bottom plate;
- S2: sliding the mounting pads into the first grooves, and arranging the reaction membrane onto the bottom plate to make the two ends of the reaction membrane be connected to the mounting pads;
- S3: upwards pulling the pipe to make the sample pad and the bonding pad slide into the first slide; pulling out the mounting pads, downwards pulling the pipe, inserting the first sealing plug, and upwards pulling the press block to make the water absorption pad slide into the second slide; pulling out the mounting pads, downwards pulling the press block, and inserting the second sealing plug; and
- S4: pushing the expansion plates to make the expansion plates be inserted into the clamping grooves.

17. A method for detecting pyrethroid pesticide residues in crops by using the device according to claim 8, the method comprising:
- S1: arranging the first mounting block and the second mounting block onto the bottom plate;
- S2: sliding the mounting pads into the first grooves, and arranging the reaction membrane onto the bottom plate to make the two ends of the reaction membrane be connected to the mounting pads;
- S3: upwards pulling the pipe to make the sample pad and the bonding pad slide into the first slide; pulling out the mounting pads, downwards pulling the pipe, inserting the first sealing plug, and upwards pulling the press block to make the water absorption pad slide into the second slide; pulling out the mounting pads, downwards pulling the press block, and inserting the second sealing plug; and
- S4: pushing the expansion plates to make the expansion plates be inserted into the clamping grooves.

18. A method for detecting pyrethroid pesticide residues in crops by using the device according to claim 9, the method comprising:
- S1: arranging the first mounting block and the second mounting block onto the bottom plate;
- S2: sliding the mounting pads into the first grooves, and arranging the reaction membrane onto the bottom plate to make the two ends of the reaction membrane be connected to the mounting pads;
- S3: upwards pulling the pipe to make the sample pad and the bonding pad slide into the first slide; pulling out the mounting pads, downwards pulling the pipe, inserting the first sealing plug, and upwards pulling the press block to make the water absorption pad slide into the second slide; pulling out the mounting pads, downwards pulling the press block, and inserting the second sealing plug; and S4: pushing the expansion plates to make the expansion plates be inserted into the clamping grooves.

\* \* \* \* \*